US010167250B2

United States Patent
Dhingra et al.

(10) Patent No.: US 10,167,250 B2
(45) Date of Patent: Jan. 1, 2019

(54) PROCESS FOR THE PREPARATION OF 2-(TRIHALOMETHYL) BENZAMIDE

(71) Applicant: SRF Limited, Gurgaon (IN)

(72) Inventors: Surender Dhingra, Gurgaon (IN); Kundan Singh Shekhawat, Gurgaon (IN); Satish Kumar, Gurgaon (IN); Kapil Kumar, Gurgaon (IN); Rajdeep Anand, Gurgaon (IN)

(73) Assignee: SRF Limited, Gurgaon (IN)

( * ) Notice: Subject to any disclaimer, the term of this patent is extended or adjusted under 35 U.S.C. 154(b) by 34 days.

(21) Appl. No.: 15/319,046

(22) PCT Filed: Jun. 16, 2015

(86) PCT No.: PCT/IN2015/000244
§ 371 (c)(1),
(2) Date: Dec. 15, 2016

(87) PCT Pub. No.: WO2015/193911
PCT Pub. Date: Dec. 23, 2015

(65) Prior Publication Data
US 2017/0129849 A1 May 11, 2017

(30) Foreign Application Priority Data
Jun. 16, 2014 (IN) .......................... 1624/DEL/2014

(51) Int. Cl.
*C07C 231/02* (2006.01)
*C07C 231/24* (2006.01)

(52) U.S. Cl.
CPC .......... *C07C 231/02* (2013.01); *C07C 231/24* (2013.01)

(58) Field of Classification Search
None
See application file for complete search history.

(56) References Cited

U.S. PATENT DOCUMENTS

2014/0378461 A1* 12/2014 O'Sullivan ............ A01N 37/18
514/247

OTHER PUBLICATIONS

Haynes et al. (CRC Handbook of Chemistry and Physics, 94 Ed., 2014, Section 15: Practical Laboratory Data, Laboratory Solvents and Other Liquid Reagents).*
Welch, et. al., "a,a,a-Trifluorotoluamides as Anticoccidial Agents," Journal of Medicinal Chemistry, 12(2), pp. 299-303. (1969).
Tsao and Eto, "Photolysis of Flutolanil Fungicide and the Effect of Some Photosensitizers," Agric. Biol. Chem., 55(3), pp. 763-768. (1991).

* cited by examiner

*Primary Examiner* — Sudhakar Katakam
*Assistant Examiner* — Jennifer C Sawyer
(74) *Attorney, Agent, or Firm* — Dinsmore & Shohl LLP

(57) ABSTRACT

The present invention relates to a process for preparation of 2-(trihalomethyl) benzamide.

4 Claims, No Drawings

PROCESS FOR THE PREPARATION OF 2-(TRIHALOMETHYL) BENZAMIDE

CROSS REFERENCE TO RELATED APPLICATIONS

This application is a 35 U.S.C. 371 national stage application of and claims priority to International Application No. PCT/IN/2015/000244 filed on Jun. 16, 2015, entitled "PROCESS FOR THE PREPARATION OF 2-(TRIHALOMETHYL) BENZAMIDE," which claims the benefit of and priority to Indian Patent Application No. 1624/DEL/2014 filed on Jun. 16, 2014, each of which is incorporated herein in their entirety by reference.

FIELD OF THE INVENTION

The present invention relates to a process for preparation of 2-(trihalomethyl) benzamide.

BACKGROUND OF THE INVENTION

The substituted benzamides, especially 2-(trihalo methyl) benzamide of Formula I, find vast usage in pharmaceutical and agrochemical field. The Welch et. al., *Journal of Medicinal Chemistry* (1969), 12(2), 299-303 describes a general process for preparation of α,α,α-trifluorotoluamides by reacting corresponding α,α,α-trifluorotoluic acid chloride with concentrated ammonium hydroxide. However, *Journal of Medicinal Chemistry* (1969), 12(2), 299-303 provides no specific example for such amidation reaction wherein the yield and purity of the product is illustrated.

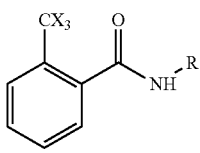

Formula I wherein X is selected from the group consisting of fluorine, chlorine, bromine and iodine; and R is hydrogen or substituted/unsubstituted $C_1$-$C_7$ alkyl group.

Despite the teaching of the prior art, the research for new preparation processes of halo alkyl substituted benzamides is still an active field and there still persists a need in the art to develop industrially scalable and economic process for the preparation of halo alkyl substituted benzamides.

OBJECTIVE OF THE INVENTION

The main objective of the present invention is to provide a process for preparation of 2-(trihalomethyl) benzamide.

SUMMARY OF THE INVENTION

An aspect of the present invention provides a process for the preparation of 2-(trihalomethyl) benzamide of Formula I,

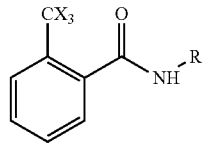

Formula I wherein X is selected from the group consisting of fluorine, chlorine, bromine and iodine; and R is hydrogen or substituted/unsubstituted $C_1$-$C_7$ alkyl group,
said process comprising;
(i) reacting a compound of Formula II with a compound of Formula III in the presence of iso-propanol to obtain a reaction mixture; and

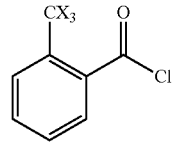

Formula II

Formula III wherein X is selected from the group consisting of fluorine, chlorine, bromine and iodine; and R is hydrogen or substituted/unsubstituted $C_1$-$C_7$ alkyl group,
(ii) isolating the compound of Formula I from the reaction mixture.

In an embodiment of the present invention, there is provided a process for the preparation of 2-(trihalomethyl) benzamide of Formula I, wherein the reaction is carried out at a temperature in the range of about −75° C. to about 25° C.

In another embodiment of the present invention, there is provided a process for the preparation of 2-(trihalomethyl) benzamide of Formula I, wherein the reaction is carried out at a time period in the range of about 10 minutes to about 6 hours.

In yet another embodiment of the present invention, there is provided a process for the preparation of 2-(trihalomethyl) benzamide of Formula I, wherein the compound of Formula I is isolated by a process selected from the group consisting of filtration, precipitation, decantation, crystallization, evaporation, layer separation and distillation or a combination thereof.

In still another embodiment of the present invention, there is provided a process for the preparation of 2-(trihalomethyl) benzamide of Formula I, wherein the reaction mixture is stirred to facilitate the reaction.

Another aspect of the present invention provides a process for the preparation of 2-(trihalomethyl) benzamide of Formula I,

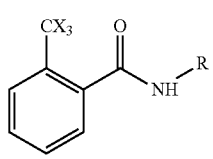

Formula I wherein X is selected from the group consisting of fluorine, chlorine, bromine and iodine; and R is hydrogen or substituted/unsubstituted $C_1$-$C_7$ alkyl group, said process comprising;

(i) reacting a compound of Formula II with a compound of Formula III in the presence of cold water to obtain a reaction mixture; and

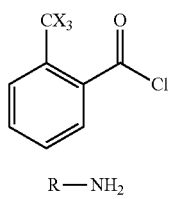

Formula II

Formula III

R—NH$_2$ wherein X is selected from the group consisting of fluorine, chlorine, bromine and iodine; and R is hydrogen or substituted/unsubstituted $C_1$-$C_7$ alkyl group, (ii) isolating the compound of Formula I from the reaction mixture.

DETAILED DESCRIPTION OF THE INVENTION

The present invention provides a process for preparation of 2-(trihalomethyl) benzamide of Formula I,

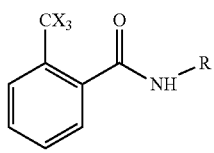

Formula I wherein X is selected from the group consisting of fluorine, chlorine, bromine and iodine; and R is hydrogen or substituted/unsubstituted $C_1$-$C_7$ alkyl group, said process comprising;

a) reacting a compound of Formula II with a compound of Formula III in the presence of iso-propanol to obtain a reaction mixture; and

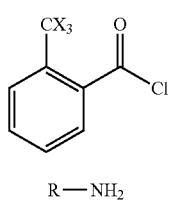

Formula II

Formula III

R—NH$_2$ wherein X is selected from the group consisting of fluorine, chlorine, bromine and iodine; and R is hydrogen or substituted/un-substituted $C_1$-$C_7$ alkyl group, b) isolating the compound of Formula I from the reaction mixture.

The present invention also provides a process for the preparation of 2-(trihalomethyl) benzamide of Formula I,

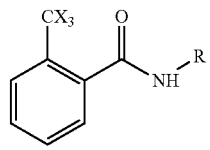

Formula I wherein X is selected from the group consisting of fluorine, chlorine, bromine and iodine; and R is hydrogen or substituted/unsubstituted $C_1$-$C_7$ alkyl group, said process comprising;

(i) reacting a compound of Formula II with a compound of Formula III in the presence of cold water to obtain a reaction mixture; and

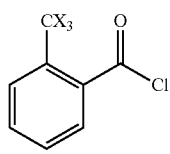

Formula II

Formula III

R—NH$_2$ wherein X is selected from the group consisting of fluorine, chlorine, bromine and iodine; and R is hydrogen or substituted/unsubstituted $C_1$-$C_7$ alkyl group, (ii) isolating the compound of Formula I from the reaction mixture.

The compound of Formula II is prepared by any method known in the art, for example, as provided in Indian Patent Application no. 3476/DEL/2011. The reaction of compound of Formula II with compound of Formula III in iso-propanol or cold water takes place at a temperature in the range of about −75° C. to about 25° C., for a time period in the range of about 10 minutes to about 6 hours. The compound of Formula III may be in liquid form or in gaseous form. The reaction mixture may be stirred to facilitate the reaction. The compound of Formula I is isolated by filtration, precipitation, decantation, crystallization, evaporation, layer separation and distillation or a combination thereof.

The compound of Formula I, obtained by the present invention, has a purity greater than about 98%, for example, greater than about 99% by HPLC.

The compound of Formula I, obtained by the present invention, is used for preparation of various agrochemical and medicinal products.

While the present invention has been described in terms of its specific embodiments, certain modifications and equivalents will be apparent to those skilled in the art and are intended to be included within the scope of the present invention.

Example

Preparation of 2-(Trifluoromethyl) Benzamide a) 2-Trifluoromethyl benzoyl chloride (50 g) and iso-propanol (400 g) were taken in a reaction vessel and ammonia gas was purged into it. The reaction was allowed to stir for 3.5 hours at a temperature in the range of −10° C. to 0° C. to facilitate the reaction. The ammonium chloride was precipitated out and the reaction mixture was filtered to obtain a filtrate. The filtrate was concentrated to obtain the compound of Formula I.
Yield: 90%
Purity (% by HPLC): 99% b) 2-Trifluoromethyl benzoyl chloride (20 g), cold water (20 g) and ammonium hydroxide (aqueous ammonia) (19.6 g) were taken in a reaction vessel and the temperature was maintained at 10° C. The reaction was allowed to stir for 3.5 hours to facilitate the reaction. The reaction mixture was then filtered and washed with water to obtain the compound of Formula I.
Yield: 90.6%
Purity (% by HPLC): >99%

What is claimed is:

1. A process for the preparation of 2-(trihalomethyl) benzamide of Formula I,

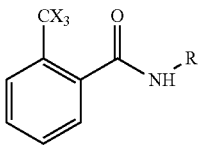

Formula I wherein X is selected from the group consisting of fluorine, chlorine, bromine and iodine; and R is hydrogen or substituted/unsubstituted $C_1$-$C_7$ alkyl group, said process comprising:

a) reacting a reaction mixture consisting of a compound of Formula II with a compound of Formula III in isopropanol to obtain the compound of Formula I; and

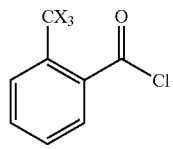

Formula II

Formula III wherein X is selected from the group consisting of fluorine, chlorine, bromine and iodine; and R is hydrogen or substituted/unsubstituted $C_1$-$C_7$ alkyl group, b) isolating the compound of Formula I formed in (a).

2. The process as claimed in claim 1, wherein the reaction is carried out at a temperature in the range of about −75° C. to about 25° C.

3. The process as claimed in claim 1, wherein the reaction is carried out at a time period in the range of about 10 minutes to about 6 hours.

4. The process as claimed in claim 1, wherein the compound of Formula I is isolated by a process selected from the group consisting of filtration, precipitation, decantation, crystallization, evaporation, and distillation or a combination thereof.

* * * * *